United States Patent [19]
Levine et al.

[11] Patent Number: 5,776,167
[45] Date of Patent: Jul. 7, 1998

[54] SYSTEM AND METHOD FOR ALLEVIATING THE EFFECTS OF PACEMAKER CROSSTALK

[75] Inventors: Paul A. Levine, Newhall; Brian M. Mann, Beverly Hills, both of Calif.

[73] Assignee: Pacesetter, Inc., Sylmar, Calif.

[21] Appl. No.: 607,501

[22] Filed: Feb. 27, 1996

[51] Int. Cl.[6] .................................................. A61N 1/362
[52] U.S. Cl. ........................................ 607/9; 607/17
[58] Field of Search ........................................ 607/9, 17

[56] References Cited

U.S. PATENT DOCUMENTS

| | | |
|---|---|---|
| 4,825,870 | 5/1989 | Mann et al. |
| 4,974,589 | 12/1990 | Sholder ............................ 128/419 PG |
| 5,366,488 | 11/1994 | Franberg et al. ........................ 607/9 |
| 5,522,857 | 6/1996 | van Krieken ........................ 607/9 |
| 5,591,214 | 1/1997 | Lu ................................ 607/9 |

FOREIGN PATENT DOCUMENTS 594957  5/1994  European Pat. Off. .................. 607/9

OTHER PUBLICATIONS

Levine,Paul A., et al., "Normal Rhythms Associated with Atrioventricular Sequential (DVI) Pacing,"Pacing Therapy,*A Guide to Cardiac Pacing for Optimum Hemodynamic Benefit*,Chapter 13, pp.191–201, (Futura Publishing Co. Mt. Kisco, New York 1983).

Levine, Paul A., et al., "Assessment and Management of Cross-Talk,"Pacing Therapy,*A Guide to Cardiac Pacing for Optimum Hemodynamic Benefit*,Chapter 17, pp. 239–251, (Futura Publishing Co., Mt. Kisco, New York 1983).

Furman,Seymour, et al., Atrioventricular Sequential Pacing and Pacemakers, *Chest*,vo. 63, No. 5, pp. 783–789, (May 1973).

Levine, Paul A., et al., "Fusion, Pseudofusion, Pseudo–Pseudofusion and Confusion: Normal Rhythms Associated with Atrioventricular Sequential DVI Pacing, "*Clinical Progress in Pacing and Electrophysiology*,vol. 1, No. 1, pp. 70–80, (1983).

Barold, Serge, et al., "Behavior of the Ventricular Triggering Period of DDD Pacemakers,"*Pace*,vol. 10, pp 1237–1252, (Nov.–Dec. 1987).

Levine, Paul A., "Normal and Abnormal Rhythms Associated with Dual–Chamber Pacemakers,"*Cardiology Clinics*, vol. 3, No.4, pp. 595–616, (Nov. 1985).

Levine, Paul A., et al., "Therapeutic and Diagnostic Benefits of International Crosstalk Mediated Ventricular Output Inhibition,"*Pace*,vol. 11, pp. 1194–1201, (Aug. 1988).

(List continued on next page.)

*Primary Examiner*—William E. Kamm
*Assistant Examiner*—Carl H. Layno

[57] ABSTRACT

Methods and apparatus are provided for alleviating the effects of crosstalk in an implantable stimulation device. An autoblanking approach is provided whereby the total blanking interval is made up of an absolute blanking interval followed by a retriggerable relative blanking interval. The implantable stimulation device sensing circuitry is disabled during the absolute blanking interval and enabled during the relative blanking intervals. If a signal is detected during a relative blanking interval, a successive relative blanking interval is initiated. If no signal is detected, then relative blanking terminates. Further, an approach for combining safety standby pacing with autoblanking is provided. If autoblanking terminates before the crosstalk sensing interval reaches a maximum blanking interval, then safety standby pacing is cancelled. Another aspect of the invention relates to monitoring the amount of time in a safety standby sensing window during which signals are detected. If signals are detected longer than a predetermined time, then a safety standby stimulation pulse is provided, otherwise, safety standby pacing is inhibited.

22 Claims, 8 Drawing Sheets

OTHER PUBLICATIONS

Castellanos, Agustin, et al., "QRS–Triggered Pacemaker and Arrhythmias Related to Early Systolic Stimulation,"*Ann. Cardiol. Angeiol*,vol. 20, No. 4, pp. 485–490, (1971).

Lemberg, Louis, M.D., et al., "Systolic and Diastolic Pacemaker Induced Repetitive Firing in the Human Heart,"*Journal of Electrocardiology*,vol.2, No. 4, pp. 353–362, (1969).

Rogel, S., et al., "Increased Excitabiltity of the Heart Induced by Electrical Stimulation in the Absolute Refractory Period,"*Chest*,vol. 60, No. 6, p. 578–582, (Dec. 1971).

Bilitch, Michael, et al., "Ventricular Fibrillation and Competitive Pacing,"*New Engalnd Journal of Medicine*,vol. 276, No. 11, pp. 598–604, (Mar. 1967).

Luceri, Richard M., et al., "Ventricular Tachycardia Produced by a Normally Functioning AV Sequential Demand (DVI) Pacemaker with Committed Ventricular Stimulation, "*The Journal of the American College of Cardiology*,vol. 1, No. 4, pp. 1177–1179, (1983).

Chardack, William M., et al., "Pacing and Ventricular Fibrillation,"*Annals New York Academy of Sciences*,pp. 919–933, (1969).

Batey, Robert L., et al., "Crosstalk and Blanking Periods in a Dual Chamber (DDD) Pacemaker: A Case Report,"*Clinical Progress in Electrophysiology and Pacing*, vol. 3, No. 4, pp. 314–318, (1985).

Barold, Serge, et al., "Characterization of Pacemaker Arrhythmias Due to Normally Functioning AV Demand (DVI) Pulse Generators,"*Pace*,vol.3, pp. 712–723, (Nov.–Dec. 1980).

Barold, Serge, et al., "Interpretation of Electrocardiograms Produced by a New Unipolar Multiprogrammable Committed AV Sequential Demand (DVI) Pulse Generator,"*Pace*, vol. 4, pp. 692–708, (Nov.–Dec. 1981).

Relay (Models 293–03 and 294–03) Intermedics Cardiac *Pulse Generator Physician's Manual*.(Intermedics. Inc., Jan. 1992).

Cosmos II (Model 284–05) Intermedics Cardiac Pulse *Generator Physician's Manual*,(Intermedics, Inc., Oct. 1988).

SYSTEM AND METHOD FOR ALLEVIATING THE EFFECTS OF PACEMAKER CROSSTALK

FIELD OF THE INVENTION

This present invention relates to methods and apparatus for alleviating the effects of crosstalk in dual-chamber pacemakers, and more particularly to methods and apparatus for providing improved autoblanking and safety standby pacing.

BACKGROUND OF THE INVENTION

A variety of pacemakers are presently available that apply electrical pulses to a patient's heart in order to maintain a healthy heart rhythm. Modern pacemakers contain sensing circuitry for monitoring the various heartbeat signals produced by a patient's heart and for controlling the operation of the pacemaker accordingly.

"Single-chamber" pacemakers sense heartbeat signals and apply stimulation pulses within a single-chamber of the heart, either an atrial or ventricular chamber, depending on the patient's individual condition. Other pacemakers, known as "dual-chamber" pacemakers, are capable of sensing and pacing within both the atrial chamber and the ventricular chamber. Although dual-chamber pacemakers are more complex than single-chambered pacemakers, they afford the physician considerable flexibility in treating the cardiac conditions of different patients.

In a normally functioning heart, the heart's sinus node generates electrical pulses at a heart rate appropriate for the body's current level of activity. The stimulus from the sinus node initially propagates to the atrial chambers, causing the associated atrial heart tissue to contract. The stimulus then propagates to the ventricles, causing the ventricular heart tissue to contract. The stimulation pulse generated by the sinus node and the subsequent atrial and ventricular contractions forms a complete heart contraction.

Dual-chamber pacemakers can be configured to operate in a variety of modes to ensure that the heart beats properly. In order to operate in the various pacing modes, dual-chamber pacemakers contain atrial sensing circuitry for monitoring heartbeat signals that occur in an atrium (e.g., the right atrium) and ventricular sensing circuitry for monitoring heartbeat signals in a ventricle (e.g., the right ventricle).

The signal that accompanies a natural atrial contraction is known as a P-wave. The normally occurring ventricular heartbeat signal is the R-wave. In one mode of pacing—known as demand pacing—the pacemaker applies stimulation pulses only if naturally occurring heartbeat signals are not detected within certain predetermined time intervals. If, for example, no P-wave is detected by the atrial channel sensing circuitry during an expected interval, then the pacemaker will apply a stimulation pulse to the atrium. But if a P-wave is detected within this time period, the atrial stimulation pulse is inhibited (not applied). Similarly, because a ventricular beat is expected to follow an atrial event (whether a naturally occurring or paced event), if an R-wave is not detected shortly following the atrial event, the pacemaker will apply a ventricular stimulation pulse. If an R-wave is detected during this time, however, then the ventricular stimulation pulse is inhibited. Demand pacing is physiologically beneficial for the patient, because it prevents competition between the pacemaker and the naturally occurring rhythm of the patient's heart.

Successful detection of naturally occurring cardiac events is crucial for effective demand pacing and for the operation of dual-chamber pacemakers in general. However, sometimes pacing signals generated by, for example, the atrial channel of the pacemaker may be detected by the sensing circuitry in the ventricular channel and erroneously identified as a naturally occurring event. This phenomena is commonly referred to as "crosstalk".

There are at least two types of crosstalk. The first type occurs when stimulation pulses from one chamber of the heart are conducted through the body and sensed on the opposite pacemaker channel, e.g., when the atrial and ventricular electrodes are closely coupled and/or the stimulation pulse amplitude is very large and/or the residual polarization signals following the stimulation pulse are significant. Another type of crosstalk occurs when conductor traces within the integrated circuits themselves are closely coupled. In either case, crosstalk typically occurs when the stimulation pulse is large.

For example, when a high atrial stimulation pulse is applied to the heart, this high output pulse may be detected by the ventricular sense amplifier which will identify any signal of appropriate amplitude as an R-wave and behave in accordance with that interpretation. Measures need to be taken to ensure that known, but physiologically inappropriate, signals are managed properly. Misidentification of crosstalk as an R-wave may inhibit the application of physiologically useful ventricular stimulation pulses. Consequently, crosstalk signals should be taken into account for proper pacemaker design and operation.

As used hereinafter, "crosstalk" shall include both types described above, i.e., crosstalk due to paced signals which are sensed between chambers, whether internal to the circuitry or conducted through the body, and include the residual polarization signals.

One approach for alleviating the effects of crosstalk is to disengage the sensing circuitry in the channel in which the crosstalk is anticipated for a predetermined length of time, known as a blanking interval. Thus, immediately following application of an atrial stimulation pulse, the ventricular sensing circuitry is turned off for the duration of the blanking interval. Because the ventricular sensing circuitry is inactive during this interval, the operation of the pacemaker will be unaffected by crosstalk.

Although, with this approach, the blanking interval may periodically be adjusted by a physician, for practical purposes the interval is fixed. As a result, the blanking interval is generally chosen to be "long enough" to ensure that crosstalk will not affect the pacemaker under a variety of conditions. However, a blanking interval that is too long increases the probability that a natural cardiac event (e.g., a premature ventricular contraction, or PVC) occurring during the blanking interval will not be sensed. This phenomenon is sometimes referred to as "blanking-induced undersensing". That is, natural cardiac events, such as R-waves or PVC's, are not detected due to a blanking interval that was too long. Missing a naturally occurring cardiac event may cause the pacemaker to apply an inappropriate stimulus to the heart. For example, if the pacemaker fails to detect a PVC because it occurred during the blanking interval, the pacemaker will fail to inhibit application of the ventricular stimulation pulse at the end of the AV delay. Thus, the pacemaker will apply a ventricular stimulation pulse, which pulse is not only unnecessary, but may be applied during the so-called "vulnerable period" of the cardiac cycle (near the apex of the T-wave). Pulses applied during the vulnerable period may induce an undesirable repetitive cardiac rhythm in an electrically unstable heart.

A technique known as "autoblanking" allows the crosstalk blanking interval to be reduced automatically. Autoblanking is described in commonly-assigned U.S. Pat. No. 4,974,589. As described in the '589 patent, the blanking interval is made up of one or more relatively short "basic" blanking intervals, each consisting of an "absolute" blanking interval and a "relative" blanking interval. During the absolute blanking intervals, the sensing circuitry is not enabled, which prevents crosstalk (e.g., the stimulation pulse) from being detected. During the relative blanking intervals, the sensing circuitry is enabled. If a signal is detected during a relative blanking interval (e.g., as a result of residual polarization), the signal is presumed to be crosstalk and the pacemaker initiates another basic blanking interval. Eventually, when no signal is detected for the entire length of a relative blanking interval, then it is presumed that the crosstalk signal has ended. Normal pacemaker function are allowed to resume and no further basic blanking intervals are initiated. With this approach, the total blanking interval length is equal to the sum of the lengths of the basic blanking intervals. Generally, this length is less than the length of a typical fixed blanking interval.

The autoblanking technique described in the '589 patent is generally satisfactory. However, the basic blanking intervals that are repeatedly retriggered in the approach of the '589 patent each contain an absolute blanking interval. During such absolute blanking intervals, it is not possible to monitor the cardiac signals for potential crosstalk. It is only during the relative blanking intervals that crosstalk is monitored. As a result, the approach of the '589 patent is not as efficient as it might be, because even if no signals occur for the entire length of one of the retriggered absolute blanking intervals (a situation that would indicate that the signal is no longer likely to be crosstalk so that normal operation can be resumed), it is not until an additional length of time—equal to a relative blanking interval—has elapsed that it is possible to terminate blanking.

Another approach for alleviating the effects of crosstalk is called safety standby pacing. With this approach, the duration of the conventional absolute blanking interval can be reduced to about 13 ms. This shorter blanking interval is immediately followed by an interval called the crosstalk detection window which is approximately 50 ms in length.

After an atrial stimulation pulse is applied, the ventricular sensing circuitry is disengaged for the duration of the blanking interval. During the crosstalk detection window, the ventricular sensing circuitry is active, but if a signal is detected in the window, the ventricular stimulation pulse is not inhibited. Because the signal detected in the crosstalk detection window could be an R-wave, the ventricular stimulation pulse is not applied at the programmed AV interval (e.g., 250 ms), but rather is applied after an abbreviated interval (e.g., 120 ms).

Allowing the ventricular stimulation pulse to be applied even if a signal is detected during the crosstalk detection window ensures that the output of the pacemaker will not be inadvertently inhibited by crosstalk. Thus, in the presence of high grade AV block, the patient would not be left asystolic. And, if the signal detected during the crosstalk detection window is a native R-wave, then applying the ventricular stimulation pulse at the abbreviated interval will typically cause the pulse to fall within a period in which the ventricular tissue is physiologically refractory (unresponsive to stimulus). It is therefore generally safe for the stimulation pulse to be applied at this point in the cardiac cycle. Applying the ventricular stimulation pulse at the abbreviated interval following an R-wave also ensures that the pulse is not applied during the heart's vulnerable period.

However, even with safety standby pacing the absolute blanking interval must still be chosen fairly conservatively. If the blanking interval is too short, crosstalk will repeatedly be detected during the crosstalk detection window. Each time crosstalk is detected, the pacemaker will apply the ventricular stimulation pulse at the abbreviated interval. While it is generally safe to apply the stimulation pulse at this point (because the ventricle is refractory), such a stimulation pulse results in a shortened, less hemodynamically optimum AV delay and, further, there may be circumstances in which this pulse could induce an undesirable heart arrhythmia. Furthermore, continued application of stimulation pulses at the abbreviated interval may cause concern on the part of medical personnel monitoring the patient's condition, because such abbreviated intervals are not commonly observed.

Furthermore, with known safety standby pacing systems, regardless of the length of the blanking interval, once signals are detected in the crosstalk detection window, release of the safety standby stimulation pulse is committed, even if there is a high probability that the detected signal is an R-wave. What is needed is a system which could inhibit the safety standby pacing output pulse if it is found that the signal sensed in the crosstalk detection window corresponds to a naturally occurring cardiac event.

SUMMARY OF THE INVENTION

In accordance with the principles of the present invention, methods and apparatus are provided for minimizing the undesirable effects of standard crosstalk protection circuits and techniques, while still protecting the patient from the adverse consequences of crosstalk.

One aspect of the present invention relates to an improved autoblanking technique that minimizes the total blanking interval. Immediately following (or coincident with) release of a stimulation pulse on a first channel (e.g., the atrial channel), the sensing circuitry for the second channel (e.g., the ventricular channel) is disabled for a period known as an absolute blanking interval. Contrary to existing techniques, the present invention repeatedly initiates a relative blanking interval following the initial absolute blanking period. During these relative blanking intervals the sensing circuitry is enabled. Signals detected during the relative blanking intervals are presumed to be crosstalk. When a signal is detected during one relative blanking interval, a subsequent relative blanking interval is initiated. After a complete relative blanking interval passes with no detected signals, blanking terminates. In addition, if no relative blanking interval passes without detected signals, blanking is still terminated when the total length of the blanking intervals reaches a predetermined maximum blanking interval.

An advantage of the present invention over previously known techniques (in which each retriggering of a blanking interval necessarily retriggers the application of an absolute and a relative blanking interval) is that the length of the total blanking interval is generally reduced.

Another aspect of the present invention relates to implementing an improved method of safety standby pacing in combination with autoblanking. The pacemaker performs autoblanking as long as the crosstalk persists. However, when the crosstalk sensing interval reaches a maximum blanking interval, blanking is terminated and a safety standby sensing window of (e.g., approximately 10–20 ms) is initiated.

During the safety standby sensing window, the ventricular channel is enabled so that the pacemaker can process signals on the ventricular channel. If crosstalk continues into the safety standby sensing window, a ventricular stimulation pulse is applied to the heart at an abbreviated AV interval (e.g., 100–120 ms). If an R-wave also occurs during the safety standby sensing window, the ventricular stimulation pulse is not applied during the terminal (or vulnerable) phase of the T-wave. Further, the ventricular stimulation pulse is applied when the heart is refractory, so it will not result in an evoked response. If no R-wave occurs during the safety standby sensing window, then the ventricular stimulation pulse would have been properly timed. Thus, when the crosstalk sensing interval reaches the maximum blanking interval in length, the full functionality of conventional safety standby pacing is maintained.

The primary difference between the present invention and the prior art is that in those instances in which the crosstalk sensing interval does not extend to the maximum blanking interval: (a) the length of the total blanking interval is reduced (which reduces blanking-induced undersensing), and (b) safety standby pacing is not invoked (which reduces the likelihood of confusion on the part of a medical personnel observing the operation of the pacemaker).

Another feature of the present invention relates to an improved safety standby pacing approach that may be used with either a fixed blanking interval or with autoblanking. With this approach, blanking is initiated simultaneously with the release of the atrial stimulation pulse. Regardless of the blanking technique that is employed, a safety standby sensing window is initiated upon the completion of blanking. During the safety standby sensing window, the pacemaker monitors not only the occurrence or non-occurrence of any sensed signals, but also determines the maximum length of time for which signals are present. Thus, when an R-wave occurs during the safety standby sensing window, the pacemaker determines that a signal was detected in the sensing window beginning at, for example, a time $T_1$. The pacemaker also determines when the signal ends, for example, at time $T_2$. Based on this type of measurement, the pacemaker determines the amount of time for which signals were detected during the safety standby sensing window. The pacemaker can either determine the total time period during which signals were detected, or can determine the length of the longest continuous signal that was detected.

Regardless of the method for determining the length of time (T) for which a signal was present during the safety standby sensing window, at some time prior to the time at which a safety standby stimulation pulse would otherwise be applied, a determination is made whether the time T is greater than a predetermined time limit corresponding to the width of an R-wave (e.g., approximately 50 ms). Because the blanking interval has terminated, two likely origins of signals in the safety standby pacing detection window are noise (i.e., crosstalk) and native ventricular beats. If the time T is greater than the predetermined interval (or continuous), then the signal is likely to be noise. Therefore, a safety standby stimulation pulse is applied. Applying a safety standby stimulation pulse ensures that the patient receives a needed stimulation pulse. If the time T is approximately equal to the predetermined interval, then the signal is likely to correspond to a native R-wave. Accordingly, no safety standby stimulation pulse is generated.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
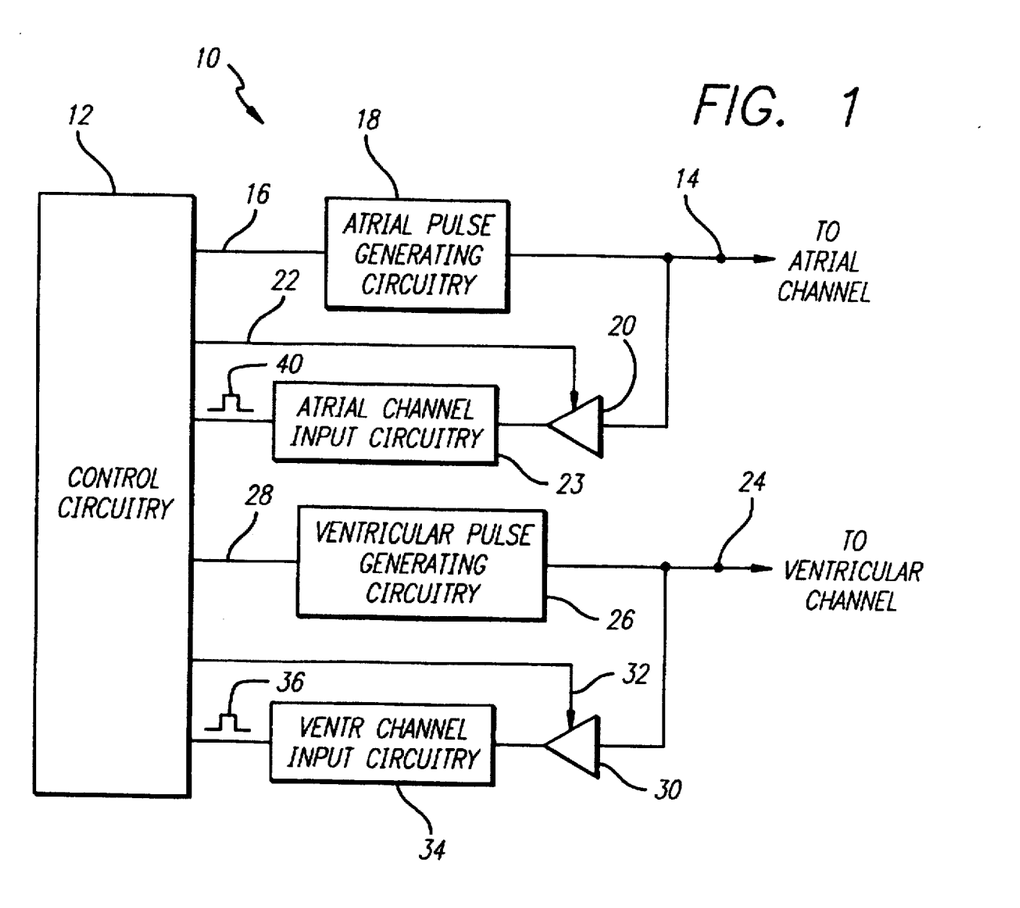
FIG. 1 is a schematic block diagram of a pacemaker constructed in accordance with the present invention.

A pacemaker 10 constructed in accordance with the present invention is shown in FIG. 1. The overall operation of the pacemaker 10 is governed by control circuitry 12, which is preferably microprocessor-based. An atrial channel electrode 14 is connected to a patient's atrium by a suitable lead (not shown). When it is desired to apply an atrial output pulse, the control circuitry 12 generates a control signal on a control line 16, which causes atrial stimulation pulse generating circuitry 18 to provide an output pulse at the electrode 14. Cardiac signals from the atrial channel are sensed using an atrial sense amplifier 20 that is enabled and disabled using a control line 22 from the control circuitry 12. The atrial channel signals are further processed by atrial channel input circuitry 23, which preferably contains conventional pacemaker bandpass and threshold detection circuitry.

The input and output circuitry for the ventricular channel generally operates in the same way as the atrial channel circuitry. Ventricular channel output pulses are generated at electrode 24 by ventricular stimulation pulse generating circuitry 26 in response to control signals received via a control line 28. The electrode 24 is connected to a patient's ventricle using an appropriate lead (not shown). Ventricular channel input signals are received via a ventricular sense amplifier 30. The control circuitry 12 enables and disables the ventricular sense amplifier 30 via a control line 32. Ventricular channel input circuitry 34 preferably contains conventional pacemaker bandpass and threshold detection circuitry.

When the patient experiences a normal ventricular contraction, an R-wave is typically sensed by the ventricular sense amplifier 30. The R-wave is provided to the ventricular channel input circuitry 34. The typical output of the ventricular channel input circuitry 34 is a pulse 36, which indicates to the control circuitry 12 the time at which the R-wave was detected. Similarly, when atrial events are detected, the atrial stimulation pulse generating circuitry 18 provides a corresponding pulse 40 to the control circuitry 12.

In normal operation of the pacemaker 10, the control circuitry 12 receives pulses, such as pulses 36 and 40, whenever cardiac events are detected. The pacemaker 10 applies corresponding atrial and ventricular stimulation pulses to the heart via the atrial and ventricular channels, as needed. The immediate effects of these pulses are generally confined to the atrium or ventricle to which the pulse is applied. occasionally, however, there can be crosstalk between the two channels (e.g., stimulation pulses and residual depolarization signals from one channel are sensed, either internally within the pacemaker or conducted within the heart. by the opposite channel).

With atrial channel to ventricular channel crosstalk, atrial stimulation pulses result in crosstalk signals on the ventricular channel that are detected by the ventricular sense amplifier 30. In order to avoid the potentially adverse effects of crosstalk, the control circuit 12 disables the ventricular sense amplifier upon release of an atrial stimulation pulse. The period, for which the ventricular sense amplifier is disabled, is known as the absolute blanking interval.

Ventricular channel to atrial channel crosstalk may also result in crosstalk on the atrial channel. which can be detected by atrial sense amplifier 20. At the time of the ventricular output pulse, the atrial sense amplifier is typically already disabled because the atrial channel has begun its refractory period. However, if sensing were enabled on the atrial channel during this refractory period, the atrial channel could likewise be disabled for an absolute blanking interval.

Thus, in the following description, illustrative embodiments of the invention are described in the context of atrial channel to ventricular channel crosstalk, although the invention is equally applicable in the context of ventricular channel to atrial channel crosstalk.

In accordance with one feature of the present invention, the blanking interval is made up of an initial absolute blanking interval (e.g., 12 ms), during which the sense amplifiers 20 and 30 are preferably disabled, followed by a retriggerable relative blanking interval (e.g., 4–8 ms each), during which signals may be sensed, but are presumed to be crosstalk. If a signal is sensed during a first relative blanking interval, the pacemaker 10 automatically restarts another relative blanking interval. When a complete relative blanking interval passes without any sensed signal, blanking is terminated. In order to minimize the phenomenon known as "blanking-induced undersensing" (i.e., in which natural cardiac events are not detected because of a lengthy crosstalk interval), blanking is also terminated whenever the total length of the crosstalk sensing interval reaches a predetermined maximum blanking interval.

Figure 2:
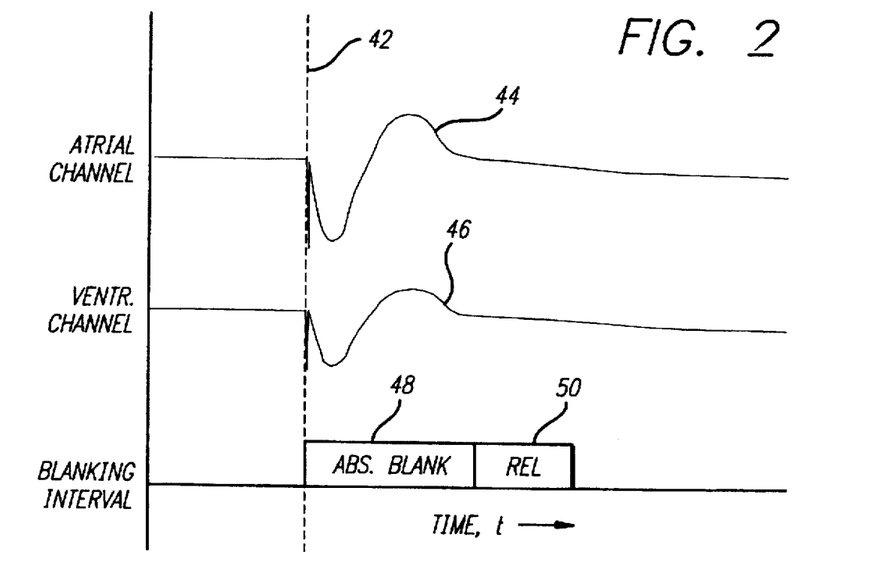
FIGS. 2 and 3 are timing diagrams illustrating the autoblanking approach of the present invention.

The autoblanking approach of the present invention is illustrated in FIGS. 2–5. As shown in FIG. 2, the release of an atrial stimulation pulse 42 results in an evoked P-wave 44. corresponding crosstalk 46 appears on the ventricular channel. At the same time that the atrial stimulation pulse 42 is released, the ventricular sense amplifier 30 is disabled by the control circuitry 12 via control signals on the control line 32. The control circuitry 12 disables the ventricular sense amplifier 30 for the duration of an absolute blanking interval 48, which is preferably about 12 ms.

After the completion of the absolute blanking interval 48, a first relative blanking period 50 is initiated during which the control circuitry 12 enables the ventricular sense amplifier 30, so that the ventricular channel input circuitry 34 can process any signals received at the electrode 24. The first relative blanking period 50 is preferably about 4 ms in length. If no signals are detected during the relative blanking interval 50, as in FIG. 2, then control circuitry 12 terminates blanking at the end of the relative blanking interval 50. The total blanking interval is equal to the sum of the absolute blanking interval 48 and the first relative blanking interval 50.

Figure 3:
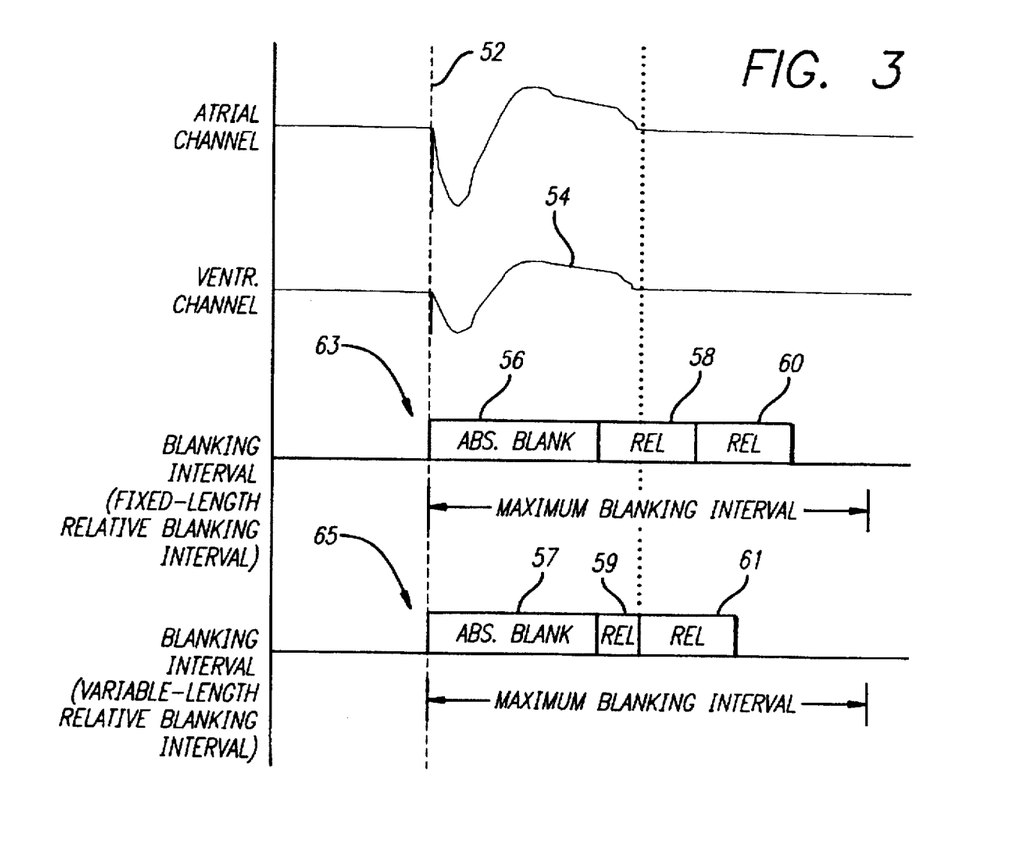

Sometimes crosstalk (e.g., residual polarization potentials) persists for a longer period of time. As shown in FIG. 3, an atrial stimulation pulse 52 results in crosstalk 54. The ventricular sense amplifier 30 is disabled for the duration of an absolute blanking interval 56. In contrast to the situation of FIG. 2, ventricular crosstalk persists during a first relative blanking interval 58. The crosstalk 54 is therefore detected during the first relative blanking interval 58. Because the blanking interval 58 is a relative blanking interval, any detected signal is presumed to be crosstalk. When a signal is detected during a relative blanking interval, the control circuitry 12 extends, or retriggers, the blanking period by another relative blanking interval 60, which is preferably approximately 4 ms in duration.

The example illustrated in the blanking interval trace 63 of FIG. 3 uses relative blanking intervals of a fixed length (e.g., 4 ms). With this approach, the control circuitry 12 waits until the entire 4 ms length of the relative blanking interval 58 passes, before commencing the relative blanking interval 60. With a clock rate of approximately 32 KHz, the 4 ms relative blanking period 58 lasts approximately 128 clock cycles.

The blanking interval trace 65 in FIG. 3 illustrates an example using variable length relative blanking intervals. When the ventricular channel input circuitry 34 detects the crosstalk 54 during the first relative blanking interval 59, the control circuitry 12 extends the blanking interval by a second relative blanking interval 61, which preferably has a maximum nominal length of approximately 4 ms. In contrast to the fixed relative blanking interval example (described above), the control circuitry 12 commences the second relative blanking interval 61 immediately after the crosstalk 54 is no longer detected on the ventricular channel. The first relative blanking interval 59 is therefore terminated before reaching the end of its nominal 4 ms duration. This approach may be preferable to the fixed relative blanking interval approach in that it further minimizes the length of the total blanking interval.

Preferably, a clock rate of approximately 32 KHz is used for generating the necessary clock signals in the pacemaker 10. As typically is the case in digital systems, control signals such as the enabling or disabling control signals for the sense amplifiers 20 and 30 are preferably generated in synchronization with the signals from the clock (contained in the control circuitry 12 of FIG. 1). Generating control signals in synchronization with the clock has a negligible effect on the length of the variable relative blanking interval, because the clock period for a 32 KHz clock (31 µs) is negligible compared with the length of a typical relative blanking period.

The process of extending the blanking interval by additional relative blanking intervals (whether of fixed or variable length) preferably continues until (1) no signals are detected for an entire relative blanking interval or (2) the total duration of the blanking interval reaches a predetermined maximum blanking interval. The maximum blanking interval preferably can be adjusted to any suitable length between zero and the length of the AV delay. In the arrangement of FIG. 3, the blanking interval is terminated prior to reaching the predetermined maximum blanking interval because no signals were detected on the ventricular channel for the final relative blanking interval.

One advantage of the autoblanking arrangement of the present invention over the autoblanking arrangement described in the above-mentioned U.S. Pat. No. 4,974,589, is that with the present approach, only the relative blanking interval is retriggered. With the arrangement of the '589 patent, whenever a signal is detected during a relative blanking interval, both a new absolute blanking interval and a new relative blanking interval are retriggered. But because no signals can be detected during the absolute blanking intervals of the '589 patent, the total length of the blanking interval may be unnecessarily long.

With the present autoblanking approach, as soon as a complete relative blanking interval passes without a signal being detected, blanking is terminated. Thus, for given absolute and relative blanking intervals, the present autoblanking technique will generally result in shorter total blanking intervals than the technique of the '589 patent. Shorter total blanking intervals are desirable, because they reduce the risk of blanking-induced undersensing.

Figure 4:
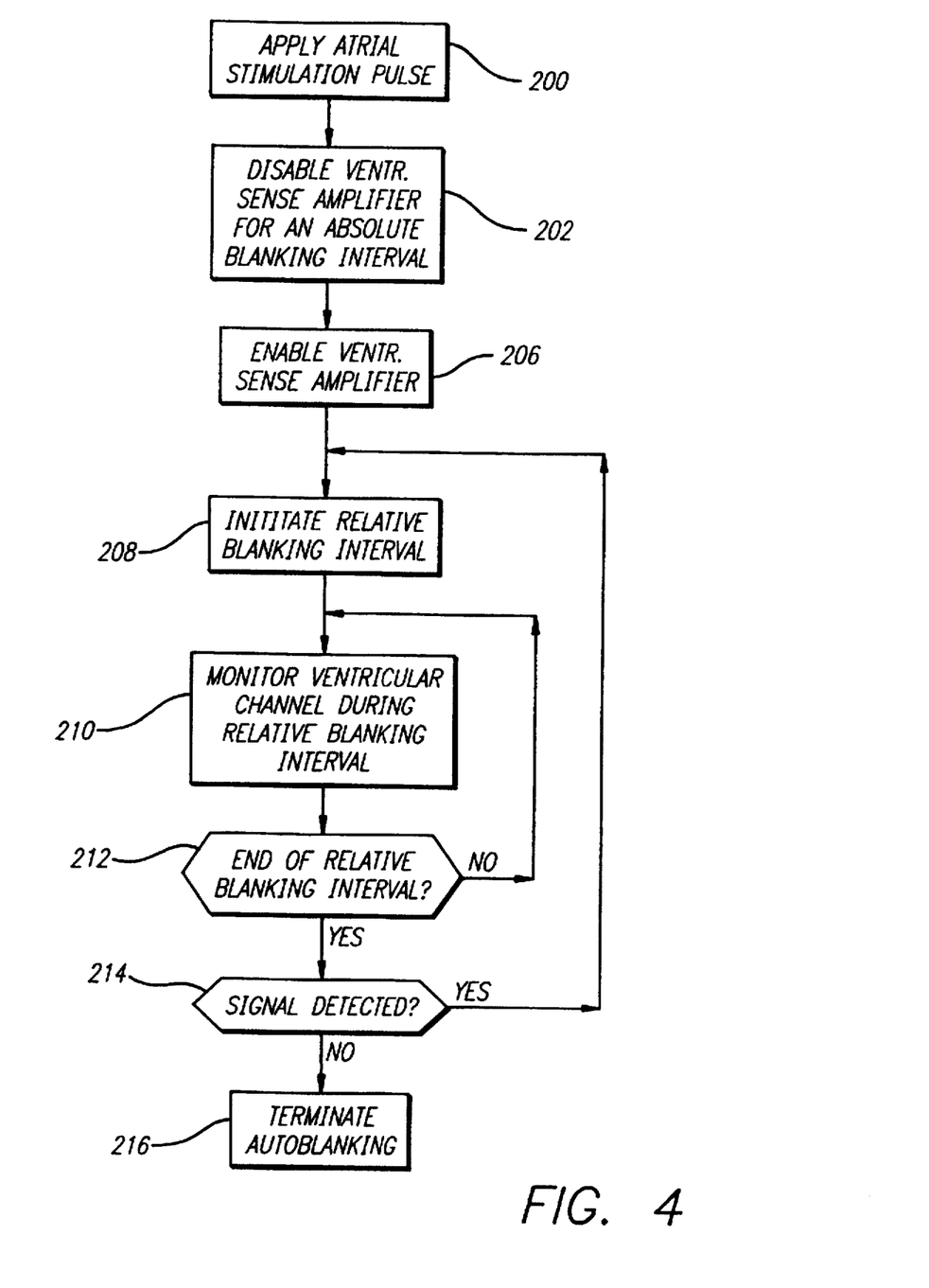
FIGS. 4 and 5 are flowcharts further illustrating the autoblanking approach of FIGS. 2 and 3.
Figure 5:
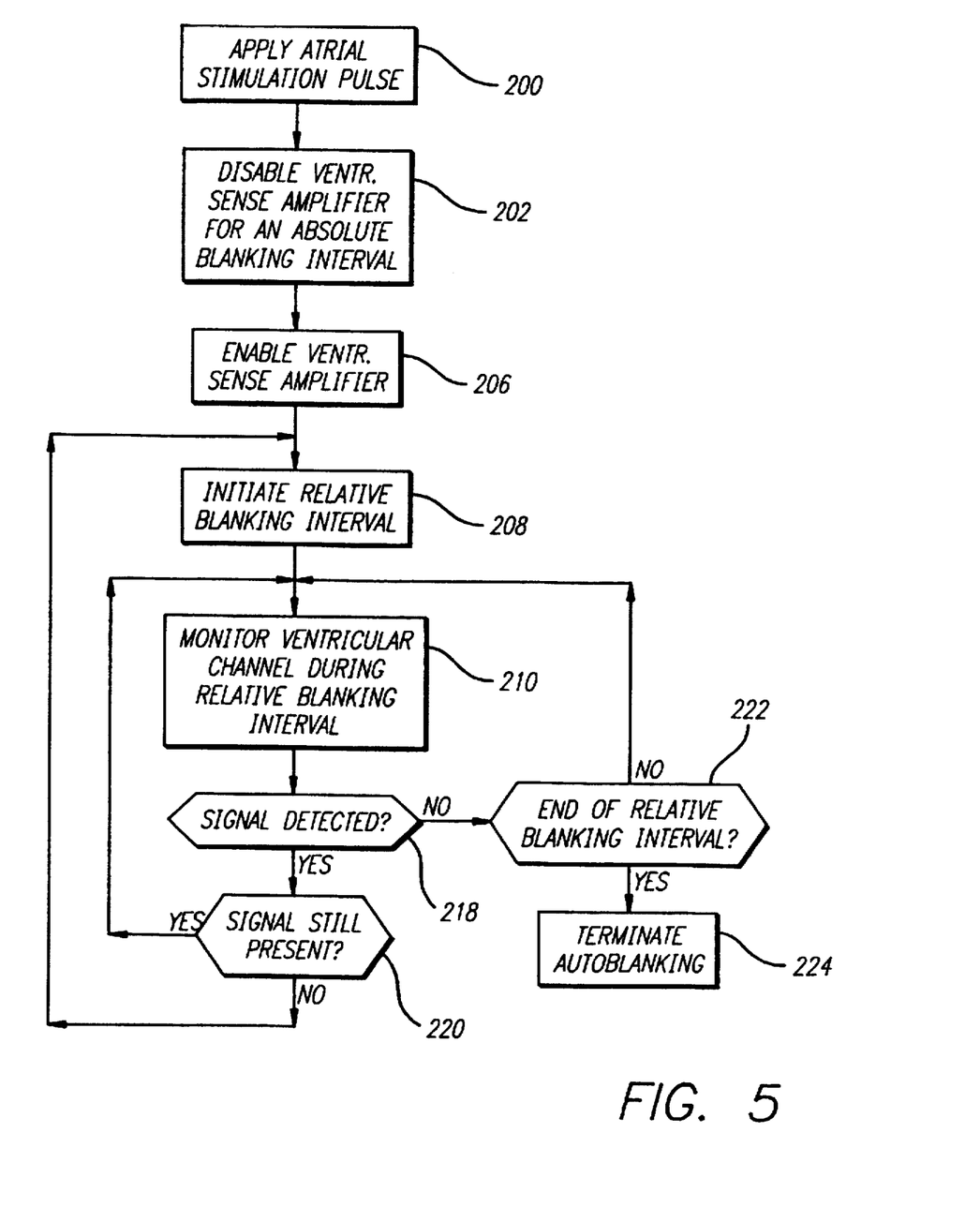

The autoblanking approach of FIGS. 2 and 3 is further illustrated in the flowcharts of FIGS. 4 and 5. Autoblanking using fixed length relative blanking intervals (trace 63, FIG. 3) is illustrated in FIG. 4. At step 200, an atrial stimulation pulse is applied to the patient's heart via the atrial stimulation pulse generating circuitry 18. The ventricular sense amplifier 30 is then disabled at step 202 for the length of the absolute blanking interval. At step 206, the ventricular sense amplifier 30 is enabled. At step 208, a relative blanking interval is initiated. For the duration of the relative blanking interval, the ventricular sense amplifier 30 and the ventricular channel input circuitry 34 monitor the signals on the ventricular channel (steps 210, 212). At test 214, the control circuitry 12 determines whether any signals were detected during the relative blanking interval. If a signal was detected, then control returns to step 208 and another relative blanking interval is initiated. If not, then an entire relative blanking interval has passed without a signal being detected and autoblanking is therefore terminated at step 216.

Autoblanking using variable length relative blanking intervals (trace 65, FIG. 3) is further illustrated in the flowchart of FIG. 5. Similar to the description above for the fixed interval approach, at step 200, an atrial stimulation pulse is applied to the patient's heart. The ventricular sense amplifier 30 is then disabled at step 202 for the length of the absolute blanking interval. At step 206, the ventricular sense amplifier 30 is enabled. At step 208, a relative blanking interval is initiated. At step 210 the ventricular sense amplifier 30 and the ventricular channel input circuitry 34 monitor the signals on the ventricular channel (step 210).

However, in this embodiment, the control circuitry 12 does not wait until the end of the relative blanking interval before checking to see if a signal has been detected. Once a signal is detected during the relative blanking interval, at step 218, then another test is done at step 220 to determine when the signal is no longer present. If the signal is still present, the system continues to monitor until the signal is gone (steps 210, 218 and 220).

Once the signal is no longer present, then control passes to step 208 and another relative blanking interval is initiated. The ventricular channel is monitored using the ventricular sensing amplifier 30 and the ventricular channel input circuitry 34 at step 210.

If the signal ceases to be present at step 218, then a determination is made as to whether the end of the relative blanking interval has been reached at step 222. The system will continue to monitor the relative blanking interval until the relative blanking interval has ended without detecting the presence of the crosstalk signal (steps 210, 218 and 222), whereby autoblanking is then terminated at step 224.

Another feature of the present invention relates to safety standby pacing. Pacemakers capable of conventional safety standby pacing are well known. With such pacemakers, a special sensing window follows the predetermined absolute blanking interval. During the absolute blanking interval, all input sensing circuitry is disabled to avoid the effects of crosstalk. During the special sensing window, the detection of a signal triggers the generation of a ventricular stimulation pulse at an abbreviated AV interval, commonly in the range of 100 ms to 120 ms. Further, because the pulse is applied at an abbreviated interval, it serves as a marker to a physician that safety standby pacing is being invoked. This allows the physician to programmably shorten the length of the absolute blanking interval to more thoroughly eliminate blanking-induced undersensing, while still protecting the patient from ventricular output inhibition if cross-talk was present. Often the signal that is detected during the special sensing window corresponds to a normal cardiac event such as an R-wave. In that case, applying the ventricular stimulation pulse at the abbreviated interval ensures that the ventricular stimulation pulse is not applied during the terminal phase of a native T-wave, which is a period of the cardiac cycle in which applied pulses can cause undesirable rhythms. The ventricular stimulation pulse is typically applied during a period of the cardiac cycle in which the heart is physiologically refractory and therefore is not affected by the applied pulse. Despite the advantages of safety standby pacing, conventional safety standby pacing has engendered concern on the part of physicians. Application of the ventricular stimulation pulse at the abbreviated interval is not an infrequent occurrence (that is, it is a relatively frequent occurrence in response to late cycle PVC's), so when it does take place physicians can become confused.

In accordance with the present invention, an improved safety standby pacing mode is implemented in conjunction with, preferably, the autoblanking mode described above. The combination ensures that the blanking period is as short as possible (thereby minimizes blanking-induced undersensing) and, further, safety standby pacing is only invoked in the event that the total crosstalk blanking interval reaches a predetermined maximum blanking interval.

If the crosstalk blanking interval is terminated prior to reaching the maximum blanking interval, there is a strong likelihood that crosstalk has not occurred, because the atrial stimulation pulse, residual polarization and any evoked response that led to the crosstalk have ended. Safety standby pacing is therefore not needed. Inhibiting safety standby pacing in instances where the blanking interval is shorter than the maximum blanking interval reduces the number of times that the ventricular stimulation pulse is applied at the reduced AV interval in response to known and appropriate physiological signals. Thus, this type of safety standby pacing arouses the concern of a physician less frequently than conventional safety standby pacing.

Figure 6:
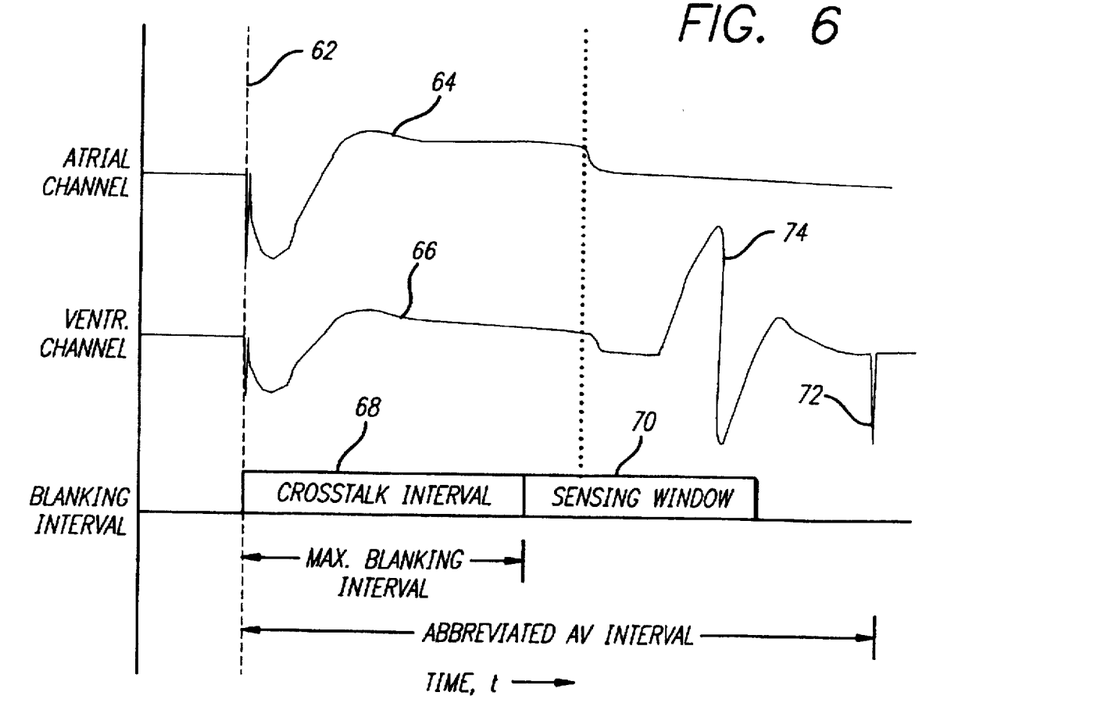
FIGS. 6 and 7 are timing diagrams illustrating safety standby pacing in conjunction with autoblanking.
Figure 7:
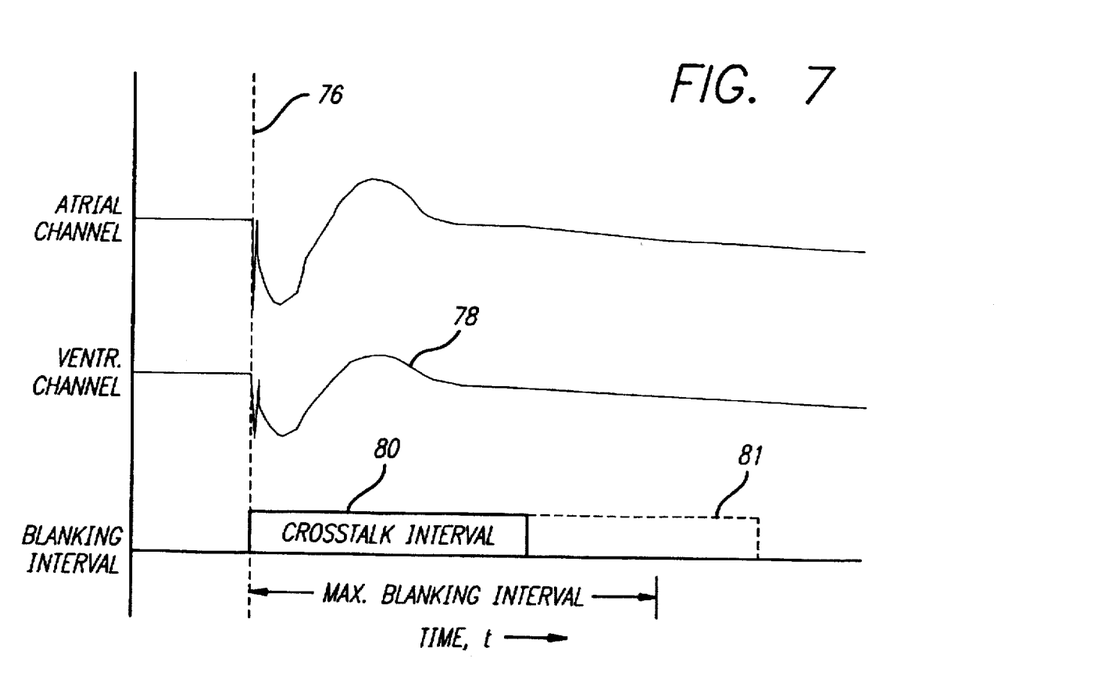
Figure 8:
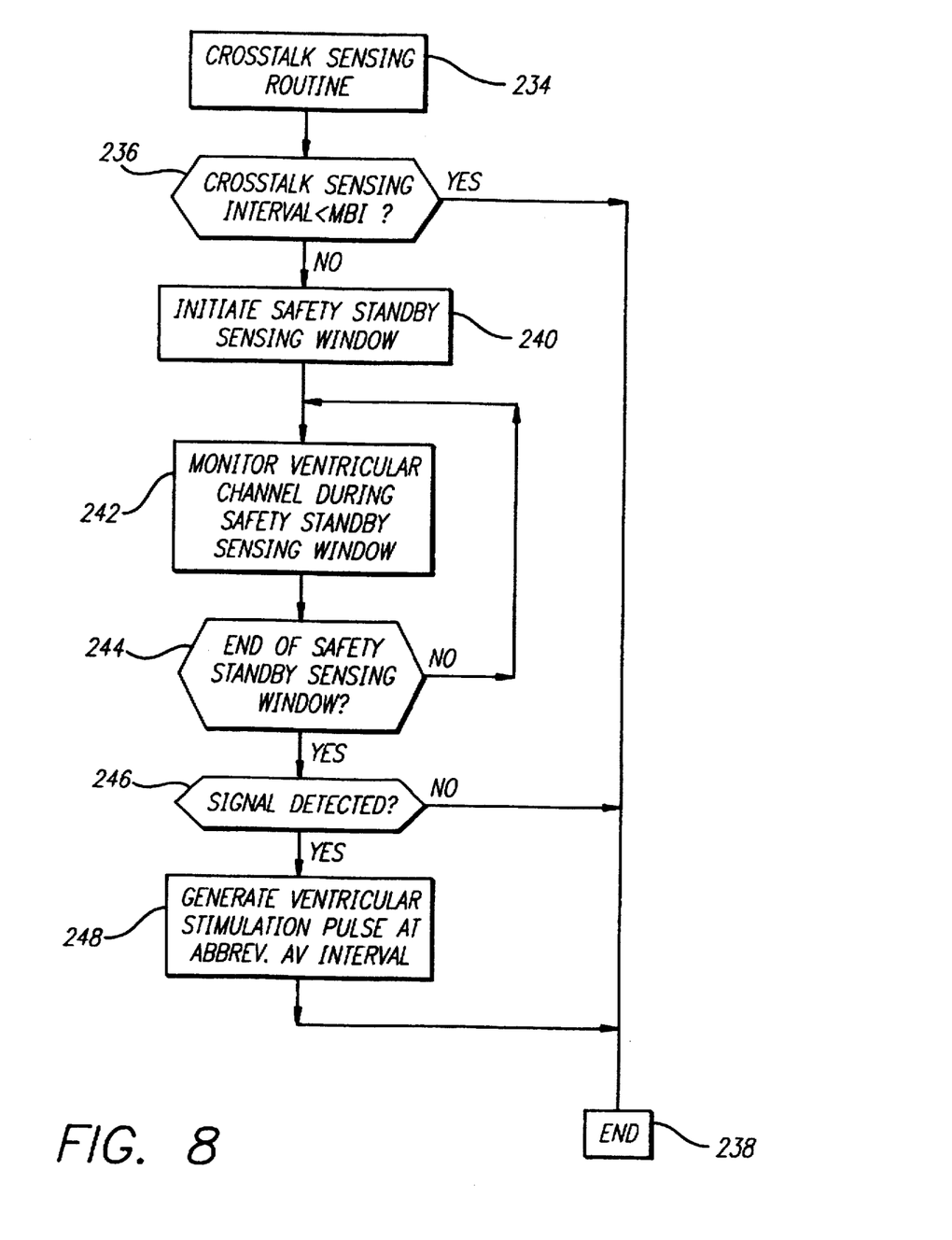
FIG. 8 is a flowchart further illustrating the safety standby pacing approach of FIGS. 6 and 7.

The safety standby pacing approach of the present invention is illustrated in FIGS. 6–8. As shown in FIG. 6, an atrial stimulation pulse 62 results in an evoked response 64. Corresponding crosstalk 66 appears on the ventricular channel. Using either an autoblanking approach such as described in the above-mentioned U.S. Pat. No. 4,974,589, or, preferably, as described above in connection with the crosstalk blanking technique of the present invention, the pacemaker performs relative blanking as long the signal continues to be detected. However, when a crosstalk sensing interval 68 reaches the maximum blanking interval, blanking interval is terminated. A safety standby sensing window 70 of, for example, approximately 10–20 ms in length, follows the crosstalk sensing interval 68. During the safety standby sensing window 70, the control circuit 12 enables the ventricular sense amplifier 30, so that the ventricular channel input circuitry 34 can process signals on the ventricular channel.

In the example shown in FIG. 6, the crosstalk 66 continues into the safety standby sensing window 70. Following detection of a signal during the safety standby sensing window 70, the control circuitry 12 applies a ventricular stimulation pulse 72 at an abbreviated AV interval (e.g., 100–120 ms). Although an R-wave 74 also occurred during the safety standby sensing window, the ventricular stimulation pulse 72 is not applied during the terminal phase of the T-wave (not shown in FIG. 6). Further, the ventricular stimulation pulse 72 is applied when the heart is refractory, so it does not result in an evoked response. If the R-wave 74 had not occurred during the safety standby sensing window 70, then the ventricular stimulation pulse 72 would have been properly timed to protect against blanking-induced undersensing. Thus, under the circumstances shown in FIG. 6, in which the crosstalk sensing interval 68 reaches the maximum blanking interval in duration, the full functionality of conventional safety standby pacing is maintained.

In those instances in which the crosstalk sensing interval does not extend to the maximum blanking interval, the length of the total blanking interval is reduced, which reduces blanking-induced undersensing. Further, safety standby pacing is not invoked, which reduces the likelihood of confusion on the part of a physician observing the operation of the pacemaker.

The operation of the pacemaker when the crosstalk sensing interval terminates before the maximum blanking interval is shown in FIG. 7. A crosstalk sensing interval 80 is initiated upon application of an atrial stimulation pulse 76. Crosstalk 78 is detected during the relative blanking intervals of the crosstalk sensing interval 80, preferably as described in the preferred embodiments of FIGS. 3–5. When crosstalk 78 is no longer detected, the crosstalk sensing interval 80 terminates. Because the crosstalk sensing interval 80 is often shorter than would be the case if a prior art blanking interval was used, blanking-induced undersensing is reduced. Further, as shown in FIG. 7, it is not necessary to invoke a safety standby pacing (illustrated as a time interval in the dotted area 81).

The safety standby pacing approach of the present invention is further illustrated in the flowchart of FIG. 8. Crosstalk sensing is carried out at step 234 using any suitable technique, such as the approach illustrated in FIGS. 2–5 or the autoblanking technique of the above-mentioned U.S. Pat. No. 4,974,589. Following crosstalk sensing, the control circuitry 12 compares the length of the total crosstalk sensing interval to a predetermined maximum blanking interval at step 236. If the crosstalk sensing interval is determined to be less than the maximum blanking interval, then safety standby pacing is not invoked, and the cycle ends at step 238. If, however, the crosstalk sensing interval reaches the maximum blanking interval, then a safety standby sensing window is initiated at step 240. The control circuitry 12 monitors the ventricular channel until the safety standby window has ended (steps 242 and 244). The control circuitry 12 then determines whether a signal was detected during the safety standby sensing window at test 246. If no signal is detected during the entire safety standby sensing window then a safety standby stimulation pulse is not applied and the cycle ends at step 238. If it is determined at test 246 that a signal was detected during the safety standby sensing window, then, at step 248, a ventricular stimulation pulse is applied to the patient's heart at an abbreviated AV interval. After the ventricular stimulation pulse is applied, the cycle ends at step 238.

Figure 9:
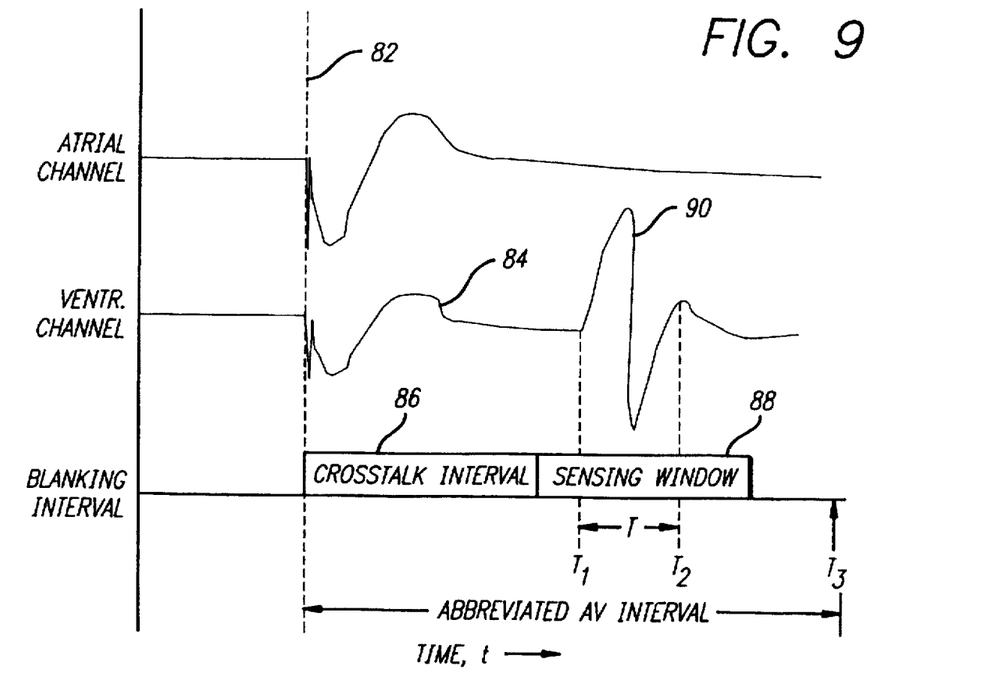
FIGS. 9 and 10 are timing diagrams illustrating the safety standby pacing approach of the present invention in which the amount of time during which signals are detected during the safety standby sensing window is determined.

Another feature of the present invention relates to an improved safety standby pacing approach that may be used with either a fixed or automatic blanking routines. This approach is described in connection with FIGS. 9–11. As shown in FIG. 9, an atrial stimulation pulse 82 results in crosstalk 84 on the ventricular channel. Simultaneous with the release of the atrial stimulation pulse 82, the control circuitry 12 initiates a crosstalk sensing interval 86 on the ventricular channel. Regardless of the blanking technique that is employed, a safety standby sensing window 88 is initiated whenever the crosstalk sensing interval 86 is completed or, as in the preferred embodiment, the crosstalk sensing interval reaches the MBI. During the safety standby sensing window 88, the control circuitry 12 monitors not only for the absence or presence of any sensed signals, it also determines the maximum length of time for which signals are present. Thus, when an R-wave 90 occurs during the safety standby sensing window 88, the control circuitry 12 determines that a signal was detected in the sensing window, and that the signal began at time $T_1$. The control circuitry 12 also determines that the signal ended at time $T_2$. Based on this type of measurement, the control circuitry 12 determines the amount of time for which signals were detected during the safety standby sensing window 88. The control circuitry 12 can use any suitable method for determining the amount of time signals are detected. For example, the control circuitry 12 can determine the total time period during which signals were detected. Alternatively, the control circuitry 12 can determine the length of the longest continuous signal that was detected. In FIG. 9, the time T is the time elapsed between the detection of the R-wave 90 at time $T_1$ and its completion at time $T_2$.

Regardless of the method for determining the length of time T for which a signal was present during the safety standby pacing detection window 88, at some time prior to time $T_3$, a determination is made whether the time T is greater than a predetermined time limit corresponding to an R-wave (e.g., approximately 50 ms). Because the crosstalk blanking interval 86 has terminated, two likely origins of signals in the safety standby pacing detection window are noise and native ventricular beats. If the time T is greater than the predetermined time limit, then the signal is likely to be noise and a safety standby stimulation pulse is applied at the abbreviated AV interval (e.g., approximately 100 ms to 120 ms) at time $T_3$. Applying a safety standby stimulation pulse ensures that the patient receives a needed stimulation pulse in the case of AV block. If an R-wave, such as R-wave 90 in FIG. 9, has a measured time, T, approximately equal to the predetermined time limit, then the system assumes that the signal is a native ventricular beat. Accordingly, application of the safety standby stimulation pulse at time $T_3$ is inhibited.

Figure 10:
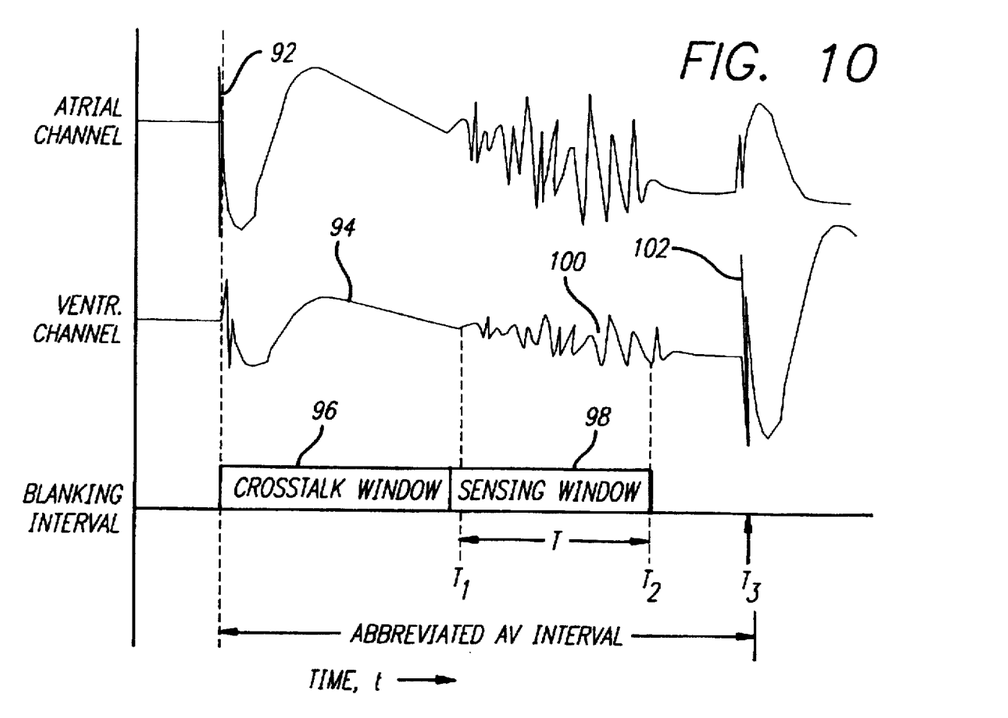

The situation in which a safety standby stimulation pulse is applied because the duration (time T) of the signal detected during the safety standby sensing window is greater than the predetermined time interval is shown in FIG. 10. An atrial stimulation pulse 92 generates crosstalk 94. The control circuitry 12 blanks out the crosstalk using either a fixed or variable length blanking interval. At the termination of the crosstalk window 96, the control circuitry 12 initiates a safety standby sensing window 98. During the safety standby sensing window 98, the control circuitry 12 enables the ventricular sense amp 30. As shown in FIG. 10, noise is present and the duration, T, of the signal 100 is greater than the predetermined time interval. Therefore, the system assumes that the signal is probably noise. Accordingly, at time $T_3$, a safety standby stimulation pulse 102 is generated.

Figure 11:
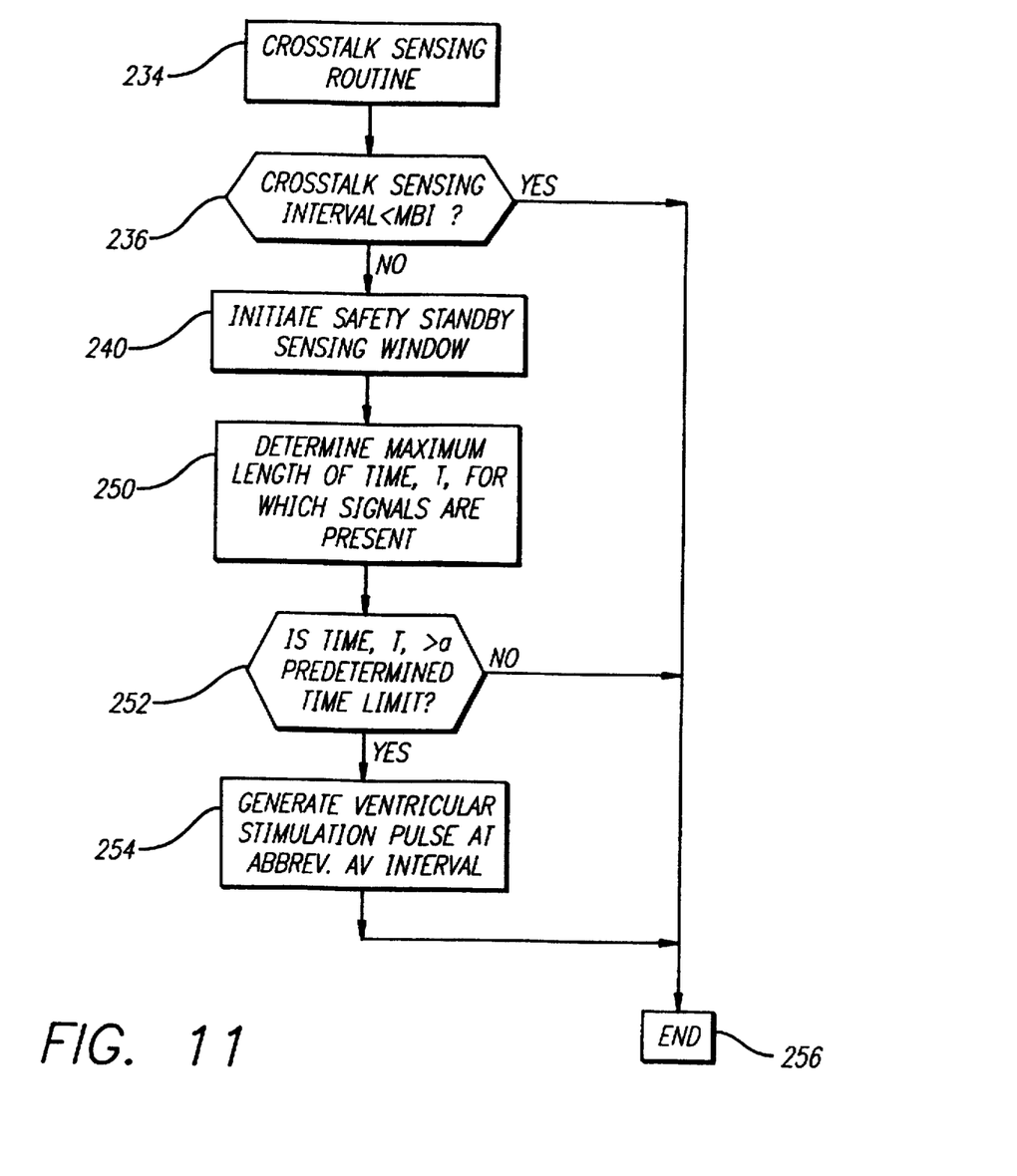
FIG. 11 is a flowchart further illustrating the safety standby pacing approach of FIGS. 9 and 10.

A flowchart of the safety standby pacing approach described in connection with FIGS. 9 and 10 is shown in FIG. 11. At step 234, a crosstalk sensing routine is performed, preferably the preferred embodiments described in FIGS. 3-5. In the preferred embodiment, the safety standby sensing window is not evoked unless the crosstalk sensing interval is greater than or equal to the Maximum Blanking Interval, MBI, as described in conjunction with FIG. 8. Thus, as determined at step 236, a crosstalk interval less than the MBI will terminate the program at step 256. A crosstalk interval greater than the MBI will initiate a safety standby sensing window at step 240. At step 250, the maximum length of time, T, for which signals were present during the safety standby sensing window is determined, using any suitable technique. At step 252, the control circuitry 12 compares the time, T, to a predetermined time limit. If the time, T, is greater than the predetermined time limit than the detected signals are likely to be noise. Since it is difficult to determine whether an R-wave occurred in the presence of noise, a safety standby stimulation pulse is applied at step 254 and the cycle ends at step 256. If T is determined at step 252 to be less than or equal to the time limit (i.e., corresponding to an R-wave), at step 258 the application of a safety standby stimulation pulse is inhibited. The cycle ends at step 256.

Thus, methods and apparatus for alleviating crosstalk in a pacemaker are provided in which pacemaker pulses applied to a patient's heart on a first pacemaker channel can result in crosstalk on a second pacemaker channel.

One skilled in the art will appreciate that the present invention can be practiced by other than the described embodiments, which are presented for the purposes of illustration and not of limitation, and the present invention is limited only by the claims that follow.

What is claimed is:

1. In an dual-chamber implantable stimulation device having an atrial and a ventricular channel, each channel having pulse generating means for generating stimulation pulses and sensing means for sensing cardiac signals in a respective chamber of the heart, an improved system for preventing crosstalk from potentially inhibiting a ventricular stimulation pulse, the improvement comprising:

control circuitry, coupled to the pulse generating means and the sensing means on each channel, for controlling the application of stimulation pulses to both chambers of the heart, wherein the control circuitry includes:

means for triggering generation of an atrial stimulation pulse at an initial time and for initiating an absolute blanking interval on the ventricular channel by disabling the ventricular sensing means for an absolute blanking interval beginning at the initial time and ending at a final time; and means for initiating, beginning at the final time, a retriggerable relative blanking interval on the ventricular channel during which the ventricular sensing means is enabled, such that if a signal is detected by the ventricular sensing means during one of the relative blanking intervals, then the control circuitry immediately initiates a successive relative blanking interval.

2. The system of claim 1, wherein the control circuitry includes means for terminating the retriggerable relative blanking interval when a total blanking interval equal to the sum of the absolute blanking interval and the relative blanking intervals reaches a predetermined maximum blanking interval.

3. The system of claim 1, wherein the relative blanking intervals are of a predetermined fixed length, such that the control circuitry initiates the successive relative blanking interval only after the one of the relative blanking intervals reaches the predetermined fixed length.

4. The system of claim 1, wherein the relative blanking intervals are of a variable length, such that the control circuitry initiates the successive relative blanking interval immediately after the input circuit ceases to detect the signal.

5. A method for autoblanking for preventing crosstalk from potentially inhibiting a ventricular stimulation pulse, the implantable stimulation device comprising a first and second channel coupled to a first and second chamber of the heart, respectively, the first channel including first pulse generating means for generating stimulation pulses and first sensing means for sensing cardiac signals, the second channel including second pulse generating means for generating stimulation pulses and second sensing means for sensing cardiac signals, the method comprising the steps of:

generating of a first stimulation pulse on the first channel at an initial time;

initiating an absolute blanking interval by disabling the second sensing means for an absolute blanking interval beginning at the initial time and ending at a final time;

initiating at the final time a retriggerable relative blanking interval on the second channel during which the second sensing means is enabled;

monitoring the second sensing means for signals on the second channel during the relative blanking interval; and initiating a successive relative blanking interval on the second channel immediately following one of the relative blanking intervals if a signal is detected by the second sensing means during one of the relative blanking intervals.

6. The method of claim 5, comprising the step of:

terminating the relative blanking intervals when a total blanking interval equal to the sum of the absolute blanking interval and the relative blanking intervals reaches a predetermined maximum blanking interval.

7. The method of claim 5, wherein the relative blanking intervals are of a predetermined fixed length, the method comprising the step of:

initiating the successive relative blanking interval only after the one of the relative blanking intervals reaches the predetermined fixed length.

8. The method of claim 5, wherein the relative blanking intervals are of a variable length, the method comprising the step of:

initiating the successive relative blanking interval immediately after the input circuit ceases to detect the signal.

9. An implantable stimulation device for alleviating crosstalk, the implantable device including a first and a second channel, each channel having pulse generating means for generating stimulation pulses and sensing means for sensing cardiac signals in a respective chamber of the heart, comprising:

control circuitry, coupled to the pulse generating means and the sensing means on each channel, for controlling the application of stimulation pulses to both chambers of the heart, wherein the control circuitry includes:

means for initiating the generation of a stimulation pulse on the first channel at an initial time;

means for initiating a retriggerable crosstalk sensing interval on the second channel beginning at the initial time, the crosstalk sensing interval having a total length which may be varied up to a predetermined maximum blanking interval;

means for initiating a safety standby sensing window immediately following the crosstalk sensing interval when the crosstalk sensing interval reaches the predetermined maximum blanking interval before terminating; and means for enabling the sensing means on the second channel during the safety standby sensing window, so that when a signal is detected on the second channel during the safety standby sensing window the control circuit initiates generation of a safety standby stimulation pulse on the second channel.

10. The implantable stimulation device of claim 9, wherein, when the crosstalk sensing interval terminates before reaching the predetermined maximum blanking interval, the control circuitry further includes means for inhibiting the generation of the safety standby stimulation pulse.

11. A method of safety standby pacing in a implantable stimulation device in which implantable stimulation device pulses applied to patient's heart on a first channel can result in crosstalk on a second channel, comprising the steps of:

initiating generation of a stimulation pulse on the first channel at an initial time;

initiating a retriggerable crosstalk sensing interval on the second channel beginning at the initial time, the crosstalk sensing interval having a total length which may be varied up to a predetermined maximum blanking interval;

initiating a safety standby sensing window immediately following the crosstalk sensing interval when the crosstalk sensing interval reaches the predetermined maximum blanking interval before terminating;

monitoring signals on the second channel during the safety standby sensing window; and initiating application of a safety standby stimulation pulse on the second channel whenever a signal is detected during the safety standby sensing window.

12. The method of claim 11, further comprising the step of:

inhibiting application of the safety standby stimulation pulse when the crosstalk sensing interval terminates before reaching the predetermined maximum blanking interval.

13. An implantable stimulation device for alleviating crosstalk which occurs when implantable stimulation device pulses applied to a patient's heart on a first implantable stimulation device channel result in signals on a second implantable stimulation device channel, comprising:

first pulse generating means for generating stimulation pulses on the first channel;

sensing means for detecting cardiac signals on the second channel; and second pulse generating means for generating stimulation pulses on the second channel; and control circuitry for controlling application of stimulation pulses, wherein the control circuitry includes:

means for initiating generation of a stimulation pulse on the first channel at an initial time;

means for initiating a blanking interval on the second channel beginning at the initial time; and means for initiating a safety standby sensing window immediately following the termination of the blanking interval;

means for enabling the sensing means during the safety standby sensing window;

means for determining an amount of time for which a signal is detected on the second channel during the safety standby sensing window;

means for initiating generation of a safety standby stimulation pulse on the second channel with the second pulse generating means when the amount of time is greater than a predetermined time interval; and means for inhibiting application of the safety standby stimulation pulse when the amount of time is less than the predetermined time interval.

14. The implantable stimulation device of claim 13, wherein the blanking interval is a fixed length blanking interval.

15. The implantable stimulation device of claim 13, wherein the blanking interval is a crosstalk sensing interval.

16. The implantable stimulation device of claim 13, wherein the control circuitry comprises means for determining the amount of time by determining a total time period during which signals were detected.

17. The implantable stimulation device of claim 13, wherein the control circuitry comprises means for determining the amount of time by determining a longest continuous detected signal length.

18. A method of safety standby pacing in an implantable stimulation device in which implantable stimulation device pulses applied to a patient's heart on a first channel can result in crosstalk on a second channel, comprising the steps of:

initiating the generation of a stimulation pulse on the first channel at an initial time;

initiating a blanking interval on the second channel beginning at the initial time;

initiating a safety standby sensing window immediately following the blanking interval;

detecting signals on the second channel during the safety standby sensing window;

determining an amount of time for which the signals are detected;

initiating the application of a safety standby stimulation pulse on the second channel when the amount of time is greater than a predetermine time interval; and inhibiting the application of a safety standby stimulation pulse on the second channel when the amount of time is less than the predetermined time interval.

19. The method of claim 18, wherein the step of initiating the blanking interval comprises the step of initiating a fixed length blanking interval.

20. The method of claim 18, wherein the step of initiating the blanking interval comprises the step of initiating an crosstalk sensing interval.

21. The method of claim 18, wherein the step of determining the amount of time comprises the step of determining a total time period during which signals were detected.

22. The method of claim 18, wherein the step of determining the amount of time comprises the step of determining a longest continuous detected signal length.

* * * * *